(12) United States Patent
Kelly et al.

(10) Patent No.: US 8,958,875 B2
(45) Date of Patent: Feb. 17, 2015

(54) STIMULATION MODE SWITCHING BASED ON TISSUE IMPEDANCE STABILITY

(75) Inventors: Kevin J. Kelly, Shoreview, MN (US); Matthew J. Michaels, St. Francis, MN (US); Gregory F. Molnar, Fridley, MN (US); Jonathan C. Werder, Corcoran, MN (US)

(73) Assignee: Medtronic, Inc., Minneapolis, MN (US)

( * ) Notice: Subject to any disclaimer, the term of this patent is extended or adjusted under 35 U.S.C. 154(b) by 1131 days.

(21) Appl. No.: 12/699,668

(22) Filed: Feb. 3, 2010

(65) Prior Publication Data

US 2011/0190851 A1    Aug. 4, 2011

(51) Int. Cl.
```
A61N 1/08      (2006.01)
A61B 5/053     (2006.01)
A61N 1/00      (2006.01)
A61N 1/365     (2006.01)
A61N 1/37      (2006.01)
```

(52) U.S. Cl.
CPC . *A61B 5/053* (2013.01); *A61N 1/00* (2013.01); *A61N 1/36521* (2013.01); *A61N 1/3702* (2013.01)
USPC ......... 607/28; 607/7; 607/8; 607/64; 600/547

(58) Field of Classification Search
USPC ........................................... 607/62; 600/547
See application file for complete search history.

(56) References Cited

U.S. PATENT DOCUMENTS

| | | | |
|---|---|---|---|
| 5,222,494 A | 6/1993 | Baker | |
| 5,836,983 A | 11/1998 | Weijand et al. | |
| 5,941,906 A | 8/1999 | Barreras et al. | |
| 7,292,889 B2 | 11/2007 | Gordon | |
| 7,359,751 B1 | 4/2008 | Erickson et al. | |
| 7,389,147 B2 | 6/2008 | Wahlstrand et al. | |
| 2005/0113880 A1* | 5/2005 | Gordon | 607/40 |
| 2005/0245977 A1 | 11/2005 | Varrichio et al. | |
| 2006/0247739 A1* | 11/2006 | Wahlstrand et al. | 607/62 |
| 2006/0253174 A1 | 11/2006 | King | |

(Continued)

FOREIGN PATENT DOCUMENTS

| | | |
|---|---|---|
| EP | 0547482 A1 | 6/1993 |
| EP | 873591 B1 | 5/2002 |
| WO | 2008049199 A1 | 5/2008 |

OTHER PUBLICATIONS

PCT/US2011/023146 International Search Report and Written Opinion mailed Apr. 6, 2011.

(Continued)

*Primary Examiner* — Christopher D Koharski
*Assistant Examiner* — Natasha Patel
(74) *Attorney, Agent, or Firm* — Withers & Keys, LLC

(57) ABSTRACT

Implantable medical devices switch from a constant current mode of operation to a constant voltage mode of operation. The switching may be based on the device determining that tissue impedance stability has occurred. The determination may be a measurement of output voltage stability of the constant current source or based on other factors such as an amount of time that has elapsed. The switching may be as the result of an externally generated request such as by a clinician via an external device. The implantable medical device may begin constant voltage mode by utilizing stimulation parameters based on those initially programmed for constant current mode and based upon a measurement of voltage amplitude being output by the constant current source prior to the switch.

24 Claims, 3 Drawing Sheets

(56) References Cited

U.S. PATENT DOCUMENTS

| | | |
|---|---|---|
| 2008/0015657 A1 | 1/2008 | Haefner |
| 2008/0300504 A1* | 12/2008 | Lefkov et al. ............... 600/547 |
| 2011/0190851 A1* | 8/2011 | Kelly et al. ................ 607/60 |

OTHER PUBLICATIONS

Benabid, et al., Chronic electrical stimulation of the ventralis intermedius nucleus of the thalamus as a treatment of movement disorders, J. Neurosurg., vol. 84, Feb. 1996, pp. 203-214.

* cited by examiner

STIMULATION MODE SWITCHING BASED ON TISSUE IMPEDANCE STABILITY

TECHNICAL FIELD

Embodiments relate to implantable devices with constant current and constant voltage modes. More particularly, embodiments relate to switching modes based on tissue impedance stability.

BACKGROUND

Implantable medical devices may provide stimulation therapy to a patient. The stimulation therapy is typically provided in the form of electrical pulses, and implantable medical leads that are attached to the implantable medical device carry the electrical pulses to stimulation sites where tissue receives the stimulation pulses.

The rate of electrical charge that reaches the tissue of interest is a primary factor in providing stimulation therapy that is effective. Initially after implant, fibrosis occurs about the stimulation electrodes of the leads at the stimulation site, and as the fibrosis progresses the tissue impedance varies. This tissue impedance instability has been addressed by the development of implantable medical devices that employ constant current pulses, as opposed to constant voltage pulses, so that the rate of delivery of charge to the tissue of interest is not adversely affected.

While the constant current mode of operation effectively deals with the tissue impedance instability that occurs until fibrosis is complete, constant current mode has drawbacks for long term use. The constant current mode of operation is inherently less efficient than a constant voltage mode, and relying on constant current over a long period will significantly reduce the service life of the implantable medical device. Furthermore, current leakage pathways may develop over time, and the rate of delivery of charge to the tissue of interest is adversely affected by the leakage pathways during constant current mode.

To address these issues resulting from constant current mode, implantable medical devices have been developed that include both a constant current mode and a constant voltage mode of operation. The device is initially programmed by a clinician to operate in a constant current mode of operation. At a later time when the clinician expects the tissue impedance to have stabilized, the clinician then re-programs the device to operate in a constant voltage mode of operation. While this process achieves the initial benefits of constant current mode with the long term benefits of constant voltage mode, an extra visit to the clinician for a re-programming session is burdensome and costly.

SUMMARY

Embodiments address issues such as these and others by providing for switching by the implantable medical device from a constant current mode of operation to a constant voltage mode of operation. The switching may be based on the device determining that tissue impedance stability has occurred. The switching may be as the result of an externally generated request such as by a clinician via an external device. The implantable medical device may begin constant voltage mode by utilizing stimulation parameters based on those initially programmed for constant current mode and based upon a measurement of voltage amplitude being output by the constant current source prior to the switch.

Embodiments include a method of providing stimulation therapy. While stimulation signals are being output from a constant current source of an implantable medical device to leads coupled to the implantable medical device, the implantable medical device detects that at least one criterion related to tissue impedance stability has been met. Upon detecting by the implantable medical device that the at least one criterion has been met, then the implantable medical device outputs stimulation signals from a constant voltage source to the leads coupled to the implantable medical device.

Embodiments include another method of providing stimulation therapy. The implantable medical device outputs stimulation signals from a constant current source to leads coupled to the implantable medical device according to at least one stimulation parameter. That tissue impedance stability has occurred is determined. After determining that tissue impedance stability has occurred, the method further involves determining by the implantable medical device an amplitude of voltage being output by the constant current source. After determining the amplitude of voltage, the implantable medical device switches to the constant voltage source. The implantable medical device outputs stimulation signals from the constant voltage source to the leads based on the determined amplitude of voltage and the at least one stimulation parameter.

Embodiments provide an implantable medical device that includes a constant current source and a constant voltage source. The implantable medical device further includes at least one electrical output connector electrically coupled to an output of the constant current source and to an output of the constant voltage source. A processor detects whether at least one criterion related to tissue impedance stability has been met. The processor establishes stimulation signals from the constant current source at the at least one electrical output connector until the at least one criterion has been met and establishes stimulation signals from the constant voltage source at the at least one electrical output connector once the at least one criterion has been met.

Embodiments provide for another implantable medical device that includes a constant current source and a constant voltage source. The implantable medical device further includes at least one electrical output connector electrically coupled to an output of the constant current source and to an output of the constant voltage source. A processor establishes stimulation signals from the constant current source at the at least one electrical output connector according to at least one stimulation parameter and maintains the stimulation signals from the constant current source until tissue impedance stability has occurred. After tissue impedance stability has occurred, the processor then determines an amplitude of voltage being output by the constant current source. After determining the amplitude of voltage, the processor then establishes stimulation signals from the constant voltage source at the at least one electrical output connector based on the determined amplitude of voltage and the at least one stimulation parameter.

Embodiments provide for a method of providing stimulation therapy. The method involves sending programming from an external device to an implantable medical device, the programming specifying constant current stimulation parameters. While stimulation signals are being output from a constant current source of the implantable medical device to leads coupled to the implantable medical device in accordance with the constant current stimulation parameters, the implantable medical device detects that at least one criterion related to tissue impedance stability has been met. Upon detecting by the implantable medical device that the at least one criterion has been met, then stimulation signals are output from a constant voltage source of the implantable medical device to the leads coupled to the implantable medical device.

Embodiments provide for a system of providing stimulation therapy. The system includes an external device that sends programming that specifies constant current stimulation parameters. An implantable medical device receives the programming and outputs stimulation signals from a constant current source according to the constant current stimulation parameters. While outputting the stimulation signals from the constant current source, the implantable medical device detects that at least one criterion related to tissue impedance stability has been met. Upon detecting that the at least one criterion has been met, the implantable medical device then outputs stimulation signals from a constant voltage source of the implantable medical device to the leads coupled to the implantable medical device.

DETAILED DESCRIPTION

Embodiments provide for an implantable medical device that has both a constant current mode and a constant voltage mode. One or more embodiments provide for the implantable medical device to switch from constant current to constant voltage mode based on tissue impedance stability such that a clinician is not required to initiate the switch. One or more embodiments provide for the implantable medical device to base the constant voltage stimulation on a measured voltage and other stimulation parameters from the constant current mode such that a clinician is not required to re-program the device for constant voltage mode.

Figure 1:
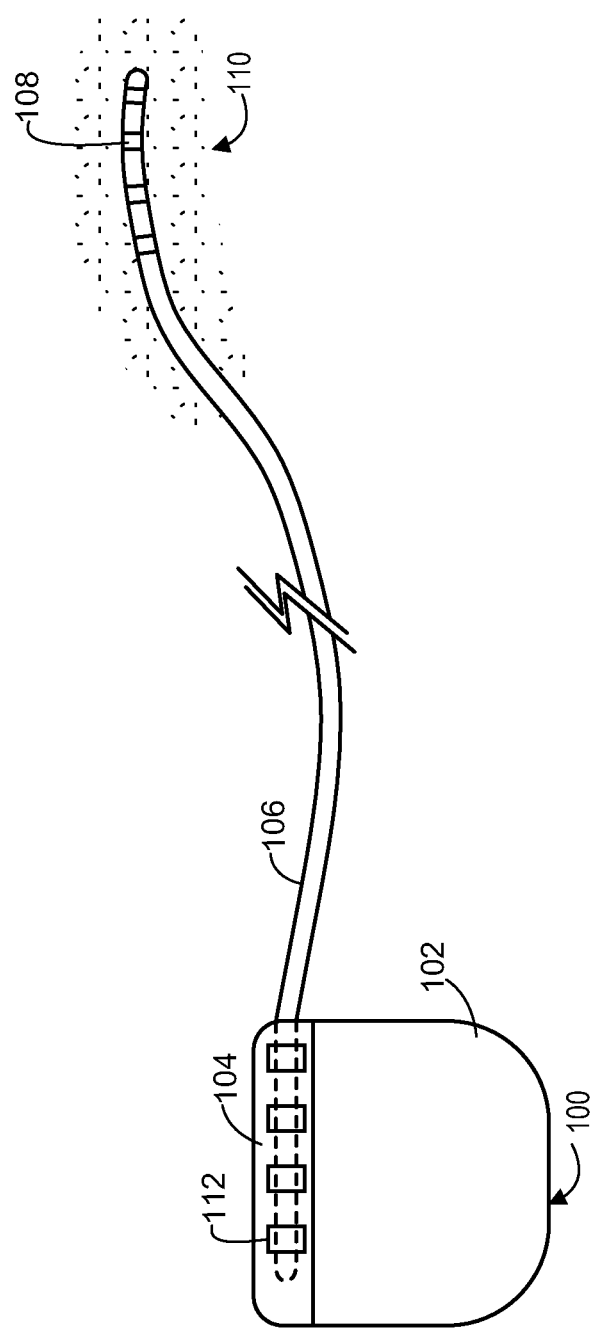
FIG. 1 shows an implantable medical device with a lead routed to a stimulation site.

FIG. 1 shows an example of an implantable medical device (IMD) 100. As examples, IMDs are used for chronic delivery of electrical stimulation therapies such as cardiac pacing, neurostimulation, muscle stimulation, or the like. In this example, the IMD 100 includes a can 102 and a connector block module 104 mounted onto the can 102. The can 102 provides a sealed enclosure for the electrical circuitry of the device 100. The connector block module 104 provides electrical connectors 112 that transfer stimulation signals from the electrical circuitry of the device 100 to electrical conductors within an implantable medical lead 106. The lead 106 has a proximal end that mounts within the connector block module 104 and has a distal end where stimulation electrodes 108 are present. Once implanted, the stimulation electrodes 108 are located at a stimulation site where the tissue 110 of interest is present.

The IMD 100 operates in a continuous current mode initially after being implanted, while fibrosis is occurring in the area of tissue 110 in proximity to the stimulation electrodes 108. The tissue impedance is unstable, and constant current stimulation is output via the connectors 112 to maintain the rate of delivery of charge to the tissue of interest 110 via the stimulation electrodes 108. Once fibrosis is complete and the tissue impedance is stable, the IMD 100 applies constant voltage stimulation that is output via the connectors 112 to deliver the charge at the desired rate to the tissue of interest 110 via the stimulation electrodes 108.

Figure 2:
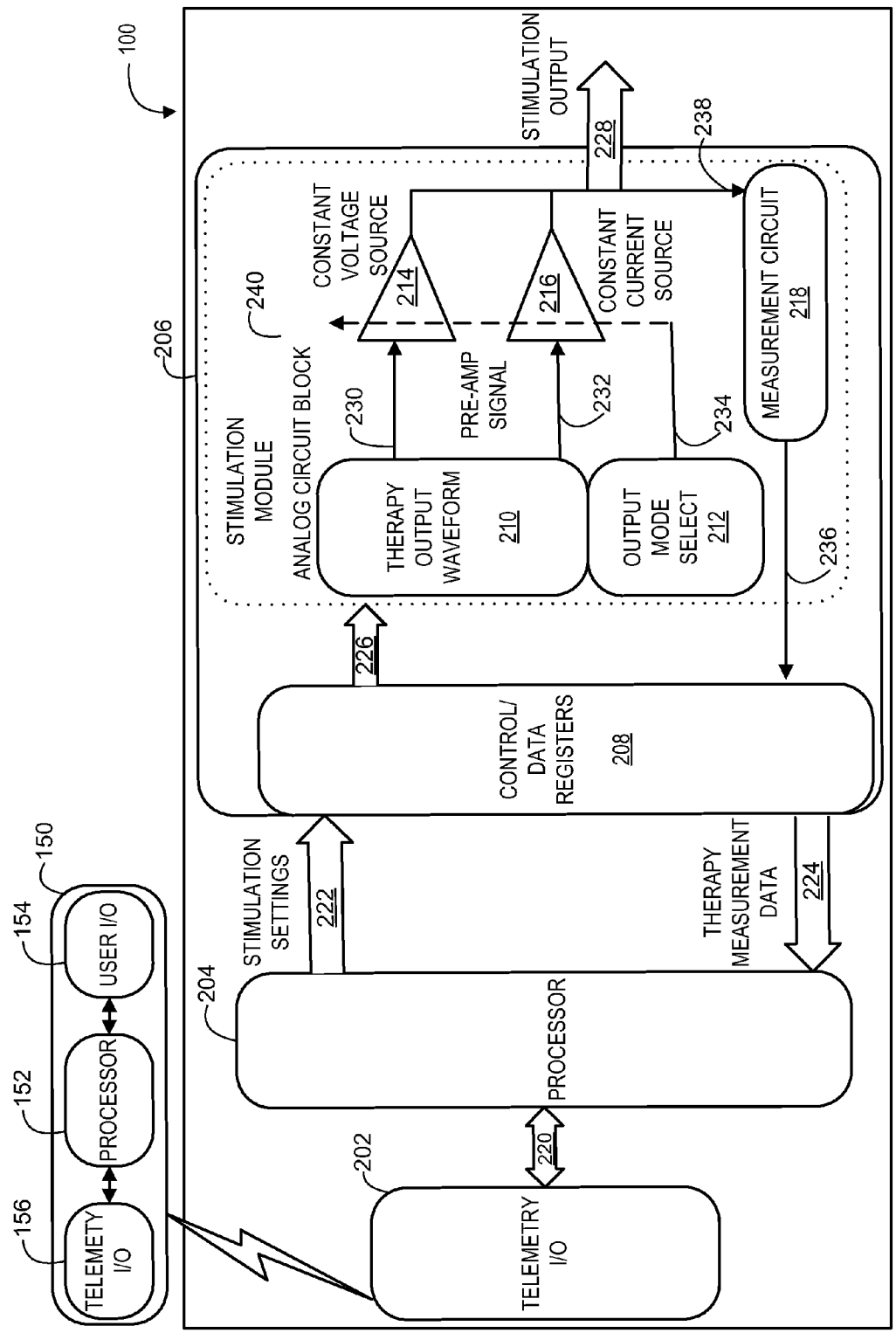
FIG. 2 shows one example of a block diagram for an implantable device that switches between constant current and constant voltage modes.

FIG. 2 shows a block diagram of one example of an IMD 100 that switches between constant current mode and constant voltage mode stimulation. The IMD 100 includes a telemetry input/output block 202 that communicates information wirelessly with an external programmer 150, which could be a clinician or patient programmer, for example. The telemetry input/output block 202 may utilize one or more various forms of telemetry including near field, arm's length, and radio frequency. The telemetry input/output block 202 exchanges information with a processor 204 via a data connection 220.

The processor 204 performs various logical operations to communicate with external devices and to control the delivery of stimulation. The processor 204 writes stimulation settings received via a telemetry session with an external device into a set of registers 208 of a stimulation module 206 over a data connection 222. The processor 204 also reads therapy measurement data from the set of registers 208 over a data connection 224. The processor 204 may be of various forms such as a dedicated purpose processor, general purpose programmable processor, application specific circuit, hardwired digital logic, and the like.

With respect to switching from constant current mode to constant voltage mode, the processor 204 may be configured to detect that tissue impedance has stabilized. The processor 204 may detect the tissue impedance stability in various ways, either by direct electrical measurement or by inferring from an indirect manner of detection. For instance, the processor 204 may rely on measurements of electrical characteristics such as the voltage being output by the constant current source at a given current amplitude. In this situation, a stable impedance may be indicated by the voltage varying by no more than a predefined amount over a predefined amount of time. As another example, the processor 204 may rely on a predefined amount of time that has elapsed since constant current therapy began to indirectly detect tissue impedance stability.

The processor 204 may write a setting to a control register of the set 208 upon time to change. Furthermore, the processor 204 may write stimulation settings for constant voltage mode to the control registers of the set 208 upon time to change. The stimulation settings being written may be based in part on the stimulation settings for constant current mode that were previously set during a programming session with the external programmer 150. For instance, the processor 204 may set a pulse rate for constant voltage mode to match that being used for constant current mode. For small pulse width therapies, such as on the order of 60-90 microseconds during constant current mode, the pulse width may also be set for constant voltage mode to match the pulse width set for the constant current mode. Additionally, the processor 204 may track charge per pulse, particularly for therapies where the width exceeds 90 microseconds during constant current mode, and may set the width for the constant voltage mode so that the charge per pulse during constant voltage mode matches the charge per pulse for the constant current mode.

The amplitude of the constant voltage may be set by the processor 204 reading a value representing the measured amplitude of voltage of the constant current source at a given point in time from a data register of the set 208. The measured amplitude of voltage may then be used to determine the amplitude of the constant voltage source. To the extent the measurement is taken at the node leading directly to the connector and the value being written corresponds to the value for that node, then the measured voltage may be written to the register. To the extent the measurement is taken at one node and the value being written to the register corresponds to a different node, then the processor 204 may perform a computation based on a function of voltage drop or gain between the two nodes to obtain the value to write to the register.

In this example, the register set 208 is accessed internally by an analog circuit block 240. The analog circuit block 240 includes a therapy output waveform generator 210. The pulse rate and width that are set in the control registers are obtained and implemented by the therapy output waveform generator 210. The therapy output waveform generator 210 sends the waveform as a signal 230/232 to the constant current source 216 and constant voltage source 214. The waveform may be of various types, such as a squarewave, rectified sinusoid, and the like.

The analog circuit block 240 also includes an output mode selection module 212. This module 212 accesses the mode setting from the control register set 208 and produces an output signal 234. The output signal 234 controls activation of the constant voltage source 214 and the constant current source 216 so that one or the other is active at any given time.

The constant voltage source 214 in this example is a voltage regulator that amplifies the voltage of the pre-amp signal based on a control value specified in the control register set 208. The constant voltage source 214, when activated by the output signal 234, provides the amplified constant voltage pulses to a stimulation output 228 where pulses are then passed to the connector block module.

The constant current source 216 in this example is a current regulator that amplifies the current of the pre-amp signal based on a control value specified in the control register set 208. The constant current source 216, when activated via the output signal 234, provides the amplified constant current pulses to the stimulation output 228 where the pulses are then passed to the connector block module.

In this example, the analog circuit block 240 also includes a measurement circuit 218 that measures an output value of the constant current and voltage sources. For example, the measurement circuit 218 may measure a voltage 238 being output by the constant voltage source 214 or the constant current source 216, whichever is active. The measurement circuit 218 then writes the measurement 236 to a data register of the set 208 so that the processor 204 may access the measurement. In addition to, or as an alternative to the voltage measurement, a measurement of charge being output to the lead per pulse may be measured and written to an available data register of the set 208. In that case, the charge per pulse in the constant current mode may be used to achieve the same charge per pulse in the constant voltage mode by adjusting pulse width for a given voltage or voltage for a given pulse width.

While FIG. 2 shows one example of components of an IMD 100 that bring about the switching between constant current and constant voltage modes, it will be appreciated that other IMD 100 configurations are possible. For instance, rather than a processor design as shown, the processor 204 could be implemented as discrete components or an application specific integrated circuit to implement a state machine.

The external programmer 150 may include components such as a processor 152, user input/output devices 154, and a telemetry module 156. The processor 152 may provide a user interface that allows a user such as a clinician or patient to set parameters for the stimulation therapy. A user may specify stimulation parameters such as the constant current parameters for pulse rate and width. The user may also specify the criterion to use for determining when to switch from constant current mode to constant voltage mode. For example, the user may specify that amount of time to delay that corresponds to tissue impedance stability, or may specify the allowable voltage variation and amount of time for determining tissue impedance stability.

The processor 152 may communicate the programming for stimulation therapy to the telemetry 202 of the IMD 100 through a telemetry module 156. The telemetry module 156 exchanges information with the telemetry module 202 of the IMD 100 via wireless signals.

While FIG. 2 also shows one example of components of the external programmer 150, it will be appreciated that other external programmer 150 configurations are possible. For instance, rather than a processor design as shown, the processor 152 could be implemented as discrete components or an application specific integrated circuit to implement a state machine.

Figure 3:
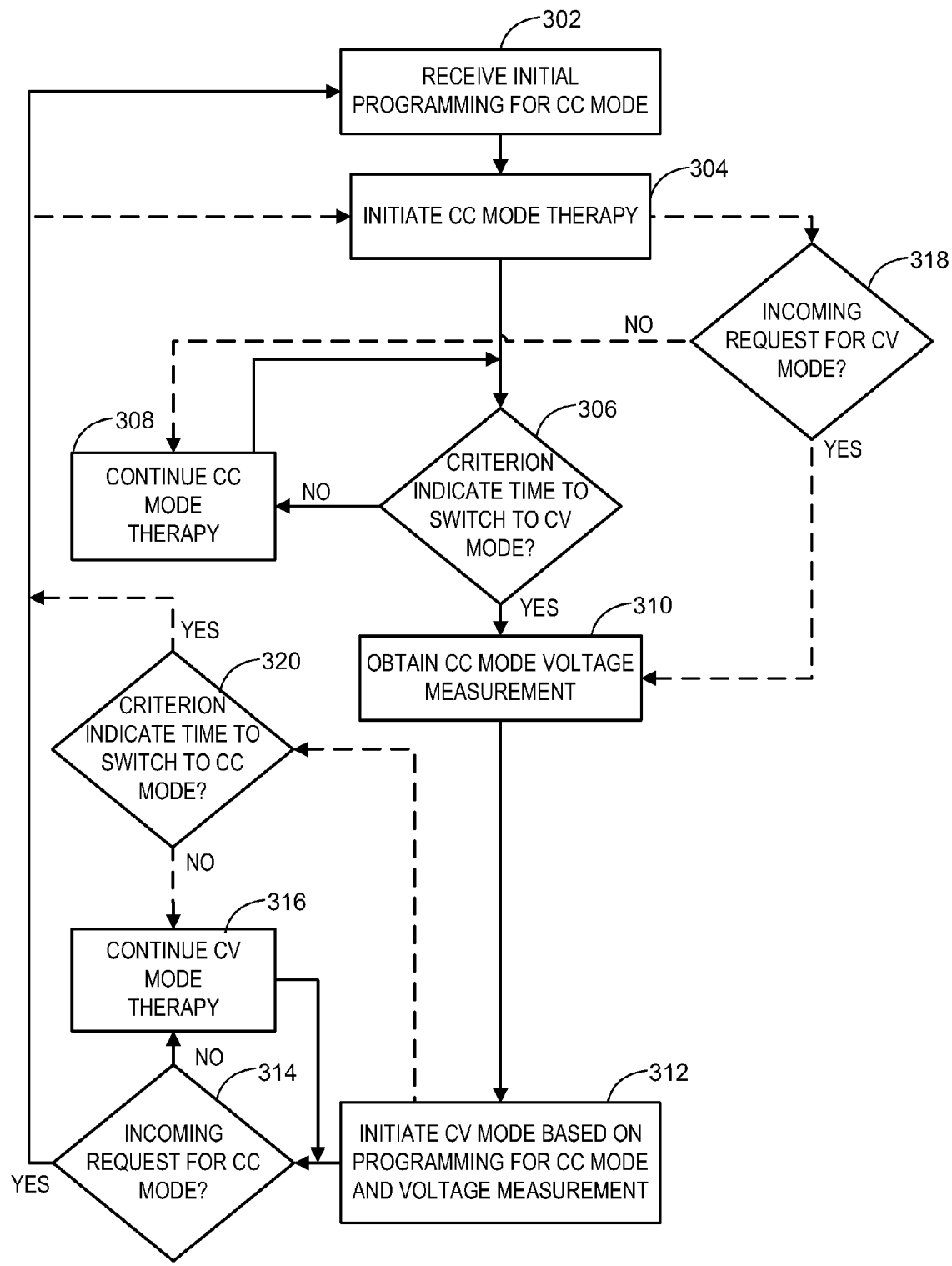
FIG. 3 shows examples of operational flow for an implantable medical device that switches between constant current and constant voltage modes.

FIG. 3 shows examples of logical operations that may be performed by the processor 204 to control whether the IMD 100 is operating in constant current (CC) or constant voltage (CV) modes. Initially, at a programming operation 302, the processor 204 receives programming for constant current mode via the telemetry 202 such as at the time of implantation of the IMD 100. This programming may specify the amplitude of the current to be provided, the rate of the pulses, the pulse width, and so forth. The processor 204 then initiates the constant current mode for the stimulation therapy at a mode operation 304. Here, the processor 204 writes the constant current stimulation parameters to the register set 208 and writes an instruction to activate the constant current source 216.

At this point, the operational flow may vary from one embodiment to the next. For instance, in one embodiment, the processor 204 may begin to detect at a query operation 306 whether at least one criterion related to tissue impedance stability has been met so that the IMD 100 may switch to constant voltage mode.

This criterion may be a measurement of the amplitude of voltage being output by the constant current source 216 varying at most by a predefined amount over a predefined amount of time. As the current is constant and the impedance of the pathway to the tissue 110 is essentially constant, this voltage measurement is directly proportional to the impedance of the tissue 110. Therefore, this voltage measurement allows a conclusion to be drawn about the stability of the tissue impedance. As a specific example, the tissue impedance may be considered stable when the measured voltage changes at most by 10% over a span of 1 week. It will be appreciated that other examples of change in stability and time are also applicable for switching modes.

This criterion may instead be a predefined amount of time that has elapsed since the constant current stimulation began. Thus, the processor 204 may track elapsed time starting from the initiation of the constant current mode at the mode operation 304. The predefined amount of time may be based on empirical data regarding when tissue impedance stability is achieved. As one example, the predefined amount of time may be set to an average time to reach tissue impedance stability, and as another example, may be set to a maximum time to reach tissue impedance stability.

It is a common assumption that deep brain stimulation with constant voltage may begin three to eight weeks after implantation. Thus, one specific example would be to maintain constant current deep brain stimulation for some period between three weeks to eight weeks and then switch to constant voltage.

Embodiments of the IMD 100 may have the capability to consider one criterion or to consider one or more of any number of criteria. Where multiple criteria are available for consideration, the IMD 100 may be programmed to utilize a particular one such as the voltage measurement or the elapsed time or to consider a combination.

When the criterion does not indicate tissue stability at the query operation 306, then the processor 204 allows constant current mode therapy to continue at therapy operation 308 by not changing the mode setting in the register set 208. When the criterion does indicate that tissue stability is achieved, then the processor 204 may begin preparing for switching to constant voltage mode at a measurement operation 310.

The processor 204 reads a present output voltage 238 being output by the constant current source at the measurement operation 310. The processor 204 may then base the constant voltage mode parameters on the constant current mode parameters and this present voltage that has been measured. As discussed above, if the value set in the register set 208 corresponds to the amplitude of output voltage 238, then the processor 204 may set the output for the constant voltage source 214 at this measured voltage. If the value written to the register set 208 for controlling the constant voltage source 214 corresponds to a voltage level prior to the output voltage 238, then the processor 204 may compute the voltage to write to the register set 208. This computation is based on the present voltage measurement and a known mathematical relationship between the output voltage 238 and the voltage corresponding to the value in the register set 208 for the constant voltage source 214.

The processor 204 may write the pulse rate and width for the constant current source to the registers of the register set 208 corresponding to the constant voltage mode, if different registers than for the constant current mode, if the same pulse rate and width are desired. However, if a different pulse rate and width are desired for constant voltage mode, then the processor 204 may apply a known mathematical relationship between the pulse rate and width for constant current mode and that for constant voltage mode. For instance, the width may be varied to achieve a matching amount of charge being provided to the tissue per pulse for a given voltage being produced by the constant voltage source 214 Alternatively, the pulse rate and width for constant voltage mode may be predefined in the register set 208 such as by the initial programming of the programming operation 302, such as for deep brain stimulation of Parkinson's Disease where the width is typically 60 to 90 microseconds with a frequency typically of 135 to 150 kilohertz.

Once the constant voltage stimulation parameters are set, the processor 204 then initiates the constant voltage mode at a mode operation 312. The processor 204 writes the constant voltage activation instruction to the register set 208 to activate the constant voltage source 214 to begin stimulation based on the stimulation parameters that have been set.

The processor 204 may then await an incoming request via a programming session through the telemetry 202 for switching back to constant current mode at a query operation 314. The processor 204 may also determine whether a criterion is met for automatically switching back to constant current mode at a query operation 320. For instance, the processor 204 may detect tissue impedance instability by detecting variation in current during constant voltage mode. As another example, the processor 204 may detect whether some event presents tissue instability. For example, activation of an unused electrode or a newly implanted electrode may call for constant current mode to that electrode.

So long as no request for constant current mode has been received and/or no detected factors call for automatically switching to constant current mode, the processor 204 allows constant voltage mode to continue at a therapy operation 316. If a request is received or a criterion for constant current is met, then the processor 204 may receive programming for the constant current mode at another occurrence of the programming operation 302. As an alternative embodiment, the processor 204 may initiate constant current mode without further programming by applying the previously programmed constant current settings. The processor 204 may then maintain constant current mode until a new criterion for constant voltage is met or as an alternative, switch to constant voltage mode once an incoming request is received to do so.

Returning to the mode operation 304, rather than proceeding to the query operation 306, one or more embodiments may provide for the processor 204 awaiting an incoming request via the telemetry 202. The processor 204 may determine at a query operation 318 whether a request for switching to constant voltage mode has been received. If no request is received, then the processor 204 allows constant current mode to continue at the therapy operation 308. If a request is received, then the processor 204 begins preparing for switching to constant voltage mode by obtaining the output voltage 238 of the constant current source at the measurement operation 310. The operations may continue as discussed above. Thus, even for embodiments where the switch to constant voltage mode is triggered by an externally generated request, the processor 204 may configure the constant voltage mode without receiving further programming.

While embodiments have been particularly shown and described, it will be understood by those skilled in the art that various other changes in the form and details may be made therein without departing from the spirit and scope of the invention.

What is claimed is:

1. A method of providing stimulation therapy, comprising:
   while stimulation signals are being output from a constant current source of an implantable medical device to leads coupled to the implantable medical device, detecting by the implantable medical device, prior to switching to a constant voltage source, that at least one criterion related to tissue impedance stability has been met; and
   upon detecting by the implantable medical device that the at least one criterion has been met, then switching from the constant current source to the constant voltage source of the implantable medical device to output stimulation signals from the constant voltage source to the leads coupled to the implantable medical device.

2. The method of claim 1, wherein the at least one criterion comprises an amplitude of voltage being output by the constant current source that varies at most by a predefined amount over a predefined length of time.

3. The method of claim 1, wherein the at least one criterion comprises a predefined amount of time that has elapsed since a reference point in time, the predefined amount of time being at least as long as an average amount of time for tissue impedance stability to be achieved.

4. The method of claim 1, further comprising measuring an amplitude of voltage of the constant current source and utilizing that measured amplitude of voltage to configure the constant voltage source.

5. The method of claim 1, further comprising switching back to the constant current source.

6. A method of providing stimulation therapy, comprising:
   outputting stimulation signals from a constant current source of an implantable medical device to leads coupled to the implantable medical device according to at least one stimulation parameter;

determining that tissue impedance stability has occurred by the implantable medical device detecting, prior to switching to a constant voltage source, that at least one criterion related to tissue impedance stability has been met;

after determining that tissue impedance stability has occurred, determining an output value of the constant current source;

after determining the output value, switching by the implantable medical device to the constant voltage source; and outputting stimulation signals from the constant voltage source to the leads coupled to the implantable medical device based on the determined output value and the at least one stimulation parameter.

7. The method of claim 6, wherein the at least one stimulation parameter comprises at least one of a rate of pulse and a width of pulse.

8. The method of claim 6, further comprising receiving at the implantable medical device an external request to switch to the constant voltage source.

9. The method of claim 6, further comprising switching back to the constant current source.

10. An implantable medical device, comprising:
a constant current source;
a constant voltage source;
at least one electrical output connector electrically coupled to an output of the constant current source and to an output of the constant voltage source; and
a processor that detects whether at least one criterion related to tissue impedance stability has been met, and the processor establishing stimulation signals from the constant current source at the at least one electrical output connector until the at least one criterion has been met and switching from the constant current source to the constant voltage source to establish stimulation signals from the constant voltage source at the at least one electrical output connector once the at least one criterion has been met.

11. The implantable medical device of claim 10, wherein the at least one criterion comprises an amplitude of voltage being output by the constant current source that varies at most by a predefined amount over a predefined length of time.

12. The implantable medical device of claim 10, wherein the at least one criterion comprises a predefined amount of time that has elapsed since a reference point in time, the predefined amount of time being at least as long as an average amount of time for tissue impedance stability to be achieved.

13. The implantable medical device of claim 10, wherein the processor obtains a measurement of an amplitude of voltage being output by the constant current source and utilizes that measurement of the amplitude of voltage to configure the constant voltage source.

14. The implantable medical device of claim 10, further comprising a telemetry module in communication with the processor and wherein the processor receives an external request from the telemetry module to switch back to the constant current source.

15. An implantable medical device, comprising:
a constant current source;
a constant voltage source;
at least one electrical output connector electrically coupled to an output of the constant current source and to an output of the constant voltage source; and
a processor that establishes stimulation signals from the constant current source at the at least one electrical output connector according to at least one stimulation parameter and maintains the stimulation signals from the constant current source until tissue impedance stability has occurred, after tissue impedance stability has occurred then determines an output value of the constant current source, and after determining the output value then switches from the constant current source to the constant voltage source to establish stimulation signals from the constant voltage source at the at least one electrical output connector based on the determined output value and the at least one stimulation parameter.

16. The implantable medical device of claim 15, wherein the at least one stimulation parameter comprises at least one of a rate of pulse and a width of pulse.

17. The implantable medical device of claim 15, wherein the processor detects, prior to establishing stimulation signals from the constant voltage source, that at least one criterion related to tissue impedance stability has been met.

18. The implantable medical device of claim 15, further comprising a telemetry module coupled to the processor and wherein the processor receives an external request to switch to the constant voltage source from the telemetry module.

19. The implantable medical device of claim 15, further comprising a telemetry module coupled to the processor and wherein the processor receives an external request to switch back to the constant current source from the telemetry module.

20. A method of providing stimulation therapy, comprising:
sending programming from an external device to an implantable medical device, the programming specifying constant current stimulation parameters;
while stimulation signals are being output from a constant current source of the implantable medical device to leads coupled to the implantable medical device in accordance with the constant current stimulation parameters, detecting by the implantable medical device that at least one criterion related to tissue impedance stability has been met, wherein the programming specifies the at least one criterion; and
upon detecting by the implantable medical device that the at least one criterion has been met, then switching from the constant current source to a constant voltage source of the implantable medical device to output stimulation signals from the constant voltage source to the leads coupled to the implantable medical device.

21. The method of claim 20, wherein the external device receives user input to create the programming.

22. A system of providing stimulation therapy, comprising:
an external device that sends programming that specifies constant current stimulation parameters;
an implantable medical device that receives the programming, that outputs stimulation signals from a constant current source of the implantable medical device according to the constant current stimulation parameters, while outputting the stimulation signals from the constant current source, detects that at least one criterion related to tissue impedance stability has been met, and upon detecting that the at least one criterion has been met, then switches from the constant current source to a constant voltage source of the implantable medical device to output stimulation signals from the constant voltage source to one or more leads coupled to the implantable medical device.

23. The system of claim 22, wherein the programming specifies the at least one criterion.

24. The system of claim 22, wherein the external device receives user input to create the programming.

* * * * *